United States Patent [19]

Pederson et al.

[11] Patent Number: 5,027,813
[45] Date of Patent: Jul. 2, 1991

[54] RATE RESPONSIVE PACEMAKER APPARATUS HAVING AN ELECTRODE INTERFACE SENSOR

[75] Inventors: Brian D. Pederson, St. Paul; John A. Hauck, Cedar, both of Minn.

[73] Assignee: Cardiac Pacemakers, Inc., St. Paul, Minn.

[21] Appl. No.: 487,918

[22] Filed: Mar. 5, 1990

[51] Int. Cl.$^5$ ............................................. A61N 1/36
[52] U.S. Cl. ............................. 128/419 PG; 128/734
[58] Field of Search ........................... 128/419 PG:734

[56] References Cited

U.S. PATENT DOCUMENTS

| | | | |
|---|---|---|---|
| 4,310,000 | 1/1982 | Lindemans | 128/419 PG |
| 4,722,342 | 2/1988 | Amundson | 128/419 PG |
| 4,823,797 | 4/1989 | Heinze et al. | 128/734 |
| 4,846,195 | 7/1989 | Alt | 128/419 PG |
| 4,907,593 | 3/1990 | Rapach et al. | 128/419 PG |

Primary Examiner—Lee S. Cohen
Assistant Examiner—Scott M. Getzow
Attorney, Agent, or Firm—Haugen and Nikolai

[57] ABSTRACT

A variable rate cardiac pacer apparatus is responsive to the physical activity of the patient. A source of alternating current carrier signals of a predetermined frequency is coupled to the pacer housing. At least one sensing electrode is coupled to the carrier signals. The sensing electrode and the pacer housing are structured and arranged to operate as a pair of interface sensing electrodes. A sense amplifier apparatus is coupled to the sensing electrodes for receiving and amplifying modulated electrical signals developed across the sensing electrodes. A demodulator circuit apparatus is structured and arranged to receive the amplified modulated carrier signal which is proportional to the impedance field around the sensing electrode. The frequency of the demodulated signal is proportional to the patient's rate of movement. A signal processing apparatus receives the demodulated signal and provides a processed signal proportional to impedance changes sensed at the interface. A rate control apparatus determines the rate at which the heart stimulating pulse will be generated in response to the processed signal.

19 Claims, 3 Drawing Sheets

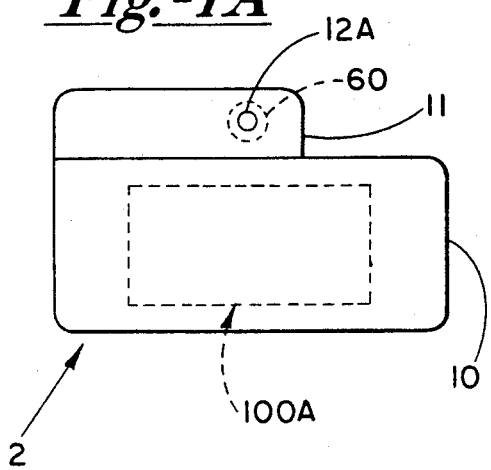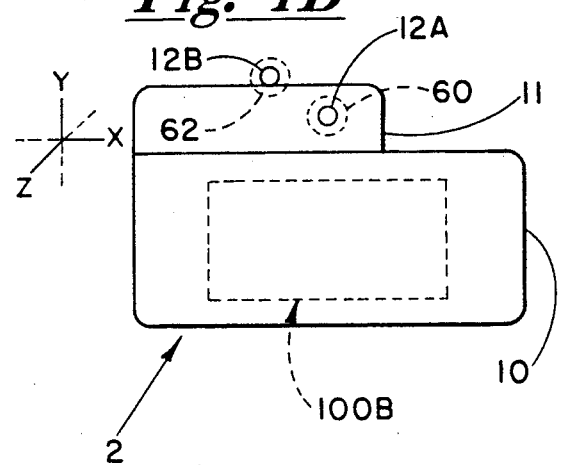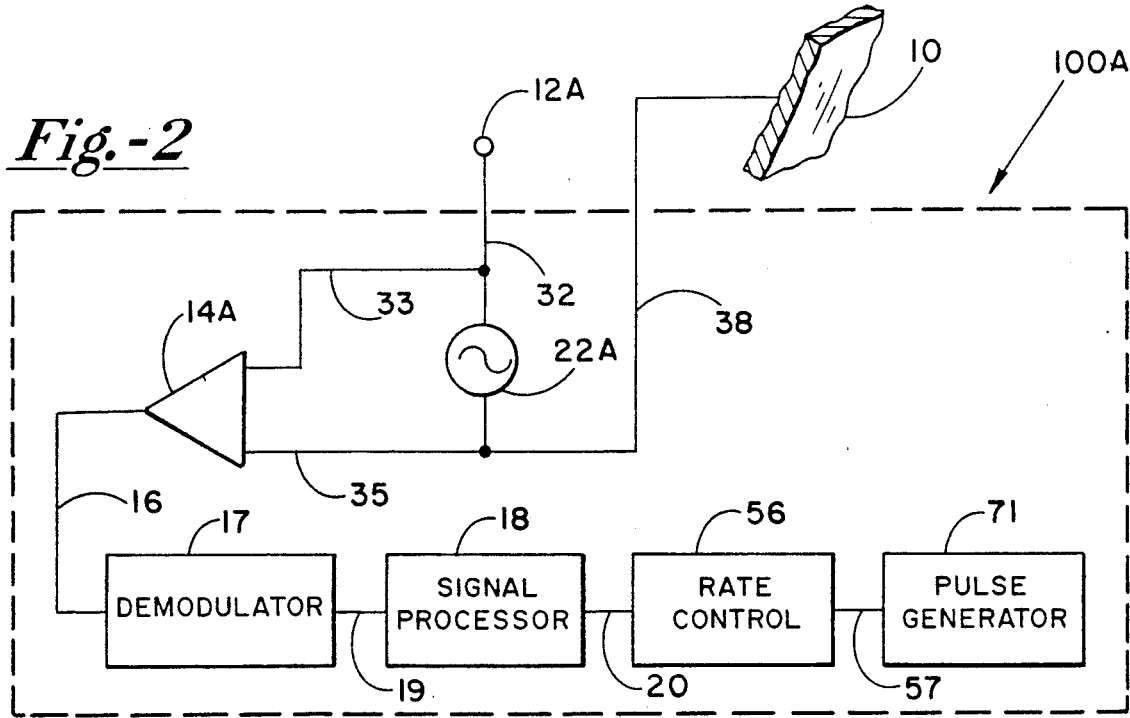

RATE RESPONSIVE PACEMAKER APPARATUS HAVING AN ELECTRODE INTERFACE SENSOR

FIELD OF THE INVENTION

This invention relates broadly to the art of implantable medical devices and, more particularly, to a variable rate cardiac pacer apparatus, including an electrode interface sensor apparatus wherein the electrode interface sensor apparatus senses changes in impedance signals at the interface of the pacer housing and the patient's body tissues, wherein the changes are indicative of relative magnitude of physical activity and are processed and used as a control signal for the rate adaptive pacemaker.

BACKGROUND OF THE INVENTION

The general activity level of a patient has been recognized in the art as useful for providing a programming signal for a variable rate cardiac pacer. For example, U.S. Pat. No. 4,140,132 suggests the use of a timing device having a self-generating voltage source to modify the constant rate of a cardiac pacemaker. That patent provides a device which embodies a cantilever suspended element which constitutes a high impedance voltage generator, such as a piezo-electric element which vibrates when subjected to motion, to provide alternating voltage from the resulting strain upon it. The cardiac pacer timing pulse rate is thereby varied as a rate of physical activity as measured by the piezo-electric element.

U.S. Pat. No. 4,428,378 suggests the use of an activity sensor mounted within a pacer. The activity sensor detects the general activity level of the patient and alters the escape interval of the pacer between a preset minimum and maximum in response to the detected activity level of the patient. U.S. Pat. No. 4,545,380 also suggests the use of a piezo-electric device for setting or adjusting parameters or functions of an implanted device such as a cardiac pacer in response to the user's impact near the implanted piezo-electric device. In yet another U.S. Pat. No. 4,771,780, it is suggested to use a motion sensor mounted within a rate responsive pacemaker. The motion sensor includes an enclosed housing having a conductive element therein that partially fills the space of a cavity within the enclosed housing. The conductive element is free to roll, flow or otherwise move around the inside of the housing in response to external forces. The types of sensors used in prior art devices are high in cost and present very complex design problems compared to the present invention.

The present invention has features and advantages not found in the prior art. This invention provides a variable rate cardiac pacer apparatus responsive to the physical activity of the patient including an electrode interface sensor apparatus which actually senses the physical movements of the pacemaker housing relative to its position in the body. The apparatus provides an impedance signal which can readily be processed into control signals for modifying the pacer pulse rates.

SUMMARY OF THE INVENTION

The present invention is directed to a variable rate cardiac pacer apparatus responsive to the physical activity of the patient wherein the pacer includes a metal housing. In one aspect of the invention, a first source of alternating current carrier signals of a first predetermined frequency in the range from about 500 to 10,000 Hertz is coupled to the pacer housing. A first sensing electrode having a sensing axis disposed primarily to sense movement in a first direction, is insulated from the pacer housing while in electrical contact with body tissues. The first sensing electrode is also coupled to the carrier signals wherein the first sensing electrode and the pacer housing are structured and arranged to operate as a first pair of interface sensing electrodes. A first sense amplifier means is coupled to the first pair of sensing electrodes for receiving and amplifying first modulated electrical signals developed across the sensing electrodes. A first demodulator circuit means for demodulating the first modulated carrier signal and recovering the first modulating signal therefrom is structured and arranged to receive the first amplified modulated carrier signal. The first modulating signal's frequency is proportional to the patient's rate of movement primarily in a first direction. A signal processing means receives the first demodulated signal and is structured and arranged to provide a processed control signal which is proportional to the demodulated signal. A rate control means receives the processed control signal, determines the rate at which the heart stimulating pulse will be generated in response to the processed control signal and provides a rate control signal to a pulse generator which is structured to provide stimulating pulses corresponding to the rate control signal.

In a further aspect of the invention, a second source of alternating current carrier signals of a second predetermined frequency in the range from 500 to 10,000 Hertz is also coupled to the pacer housing. Further, a second sensing electrode having a sensing axis arranged in a perpendicular relationship to the first sensing axis is structured and arranged to operate with the pacer housing to form a second pair of sensing electrodes wherein patient movement in a second direction is primarily sensed. Further yet, a second sense amplifier means is coupled to the second pair of sensing electrodes for receiving and amplifying a second set of modulated electrical signals developed across the second pair of sensing electrodes. The second set of amplified signals is presented to a second demodulator circuit for recovering a second modulating signal therefrom. The second modulating signal is further presented to the signal processing means for processing together with the first recovered modulating signals.

Other objects, features and advantages of the present invention will become apparent to those skilled in the art through the description of the preferred embodiment, claims and drawings herein wherein like numerals refer to like elements.

BRIEF DESCRIPTION OF THE DRAWINGS

FIG. 1A schematically shows a pacer apparatus including an interface sensor electrode provided in accordance with the teachings of the invention.

FIG. 1B schematically shows a pacer apparatus having a pair of orthogonally positioned interface sensor electrodes as provided by the present invention.

FIG. 2 schematically shows a block diagram of the circuits employed in one aspect of the invention.

DESCRIPTION OF THE PREFERRED EMBODIMENT

Figure 3:
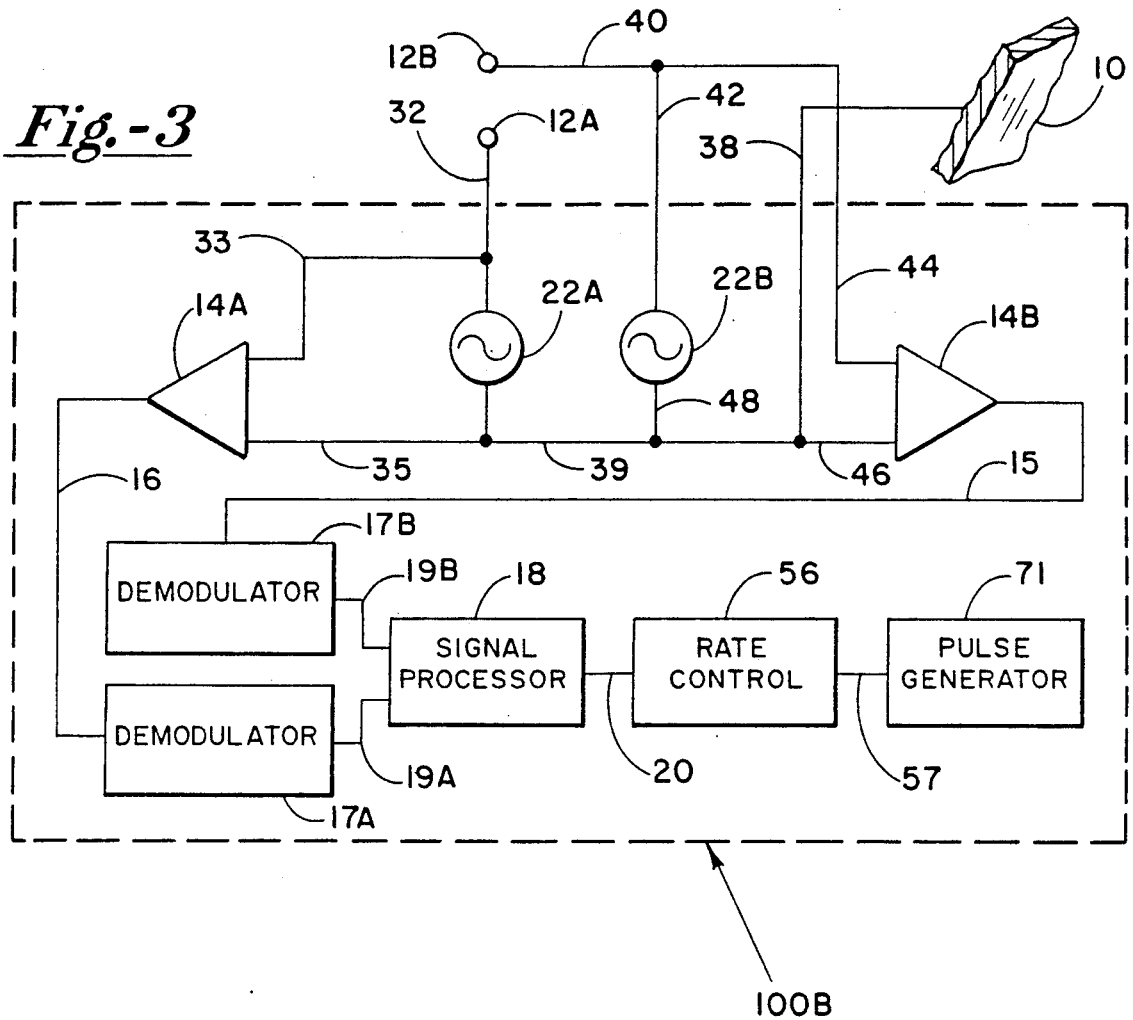
FIG. 3 shows a block diagram of the electronic circuits used in a further aspect of the invention.

Referring now to FIG. 1A, a pacer apparatus 2 including a metallic housing or can 10, a top 11, and electronic circuit 100A is shown. The pacer apparatus 2 is implanted in a patient and an electrode 12A is located proximate the pacer apparatus, but insulated from the metallic housing 10 so as to sense impedance changes in the interface area generally indicated as 60 where the pacer apparatus interfaces with the patient's body tissues. In one embodiment of the invention, the top 11 is made of an insulating material such as plastic and the interface electrode 12A is embedded in the top.

Referring now to FIG. 2, a more detailed block diagram illustrating the elements of electronic circuit 100A is shown. It will be understood that other conventional circuitry is included within the rate adaptive pacer 2, however only those elements essential to the invention have been specifically shown in the drawings so as to highlight the teachings of the present invention. Electronic circuit 100A comprises a first sense amplifier 14A having first and second inputs across which is located a first source of alternating current carrier signals 22A wherein the first current carrier signals have a first predetermined frequency. The first sensing electrode 12A is coupled by means of conductor 32 to the alternating current source 22A and by means of conductor 33 connected to conductor 32 to a first input of amplifier 14A. The second input of amplifier 14A is coupled at conductor 35 to the other side of the current source 22A and by conductor 38 to the metal housing 10 of the pacer, a portion of which is shown in FIG. 2. The output of amplifier means 14A is coupled by conductor 16 to demodulator circuit means 17 which is further coupled to signal processor means 18. Rate control means 56 is coupled to signal processor means 18 by line 20. Rate control means 56 provides a control signal via conductor 57 to pulse generator means 71. The pulse generator means 71 outputs a stimulating pulse.

Referring now to FIG. 1B an alternative embodiment of the invention is shown having at least two interface sensing electrodes 12A and 12B. 12A and 12B are structured and arranged to sense motion primarily along intersecting sensing axes and, advantageously are disposed to have their sensing axes in perpendicular relationship to each other. The small graph beside the pacer apparatus 2 indicates the standard cartesian coordinate system having X, Y and Z axes. In the example shown, the sensing electrode 12A may be disposed to sense movement primarily in the direction along the Z axis while the second sensing electrode 12B may be disposed to sense movement of the patient along the Y axis. At any given time these movements may be summed to yield a movement vector. The pacer apparatus 2, in this case, has additional circuitry to provide current sense signals from the second sensing electrode in electronic circuit 100B.

Referring now to FIG. 3, a more detailed diagram of the elements of circuit 100B is shown. The circuit is substantially similar to circuit 100A with the addition of another set of motion sensing components associated with the second interface sensing electrode. These additional components are, namely, sense amplifier means 14B, a second source of a carrier signal 22B and an additional demodulator 17B. Conductors 40, 42 and 44 couple the second electrode 12B to the second current source and second sense amplifier means. The connections of the components also found in circuit 100A are as described above. The output of sense amplifier 14B is provided to the second demodulator 17B by conductor 15 and the demodulated signals from 17A and 17B are then processed, as explained below, by the signal processor means 18, to present a processed signal proportional to the motion of the patient in two directions to the rate control means. Note that in this embodiment current carrier sources 22A and 22B preferably operate at different carrier frequencies.

Figure 4:
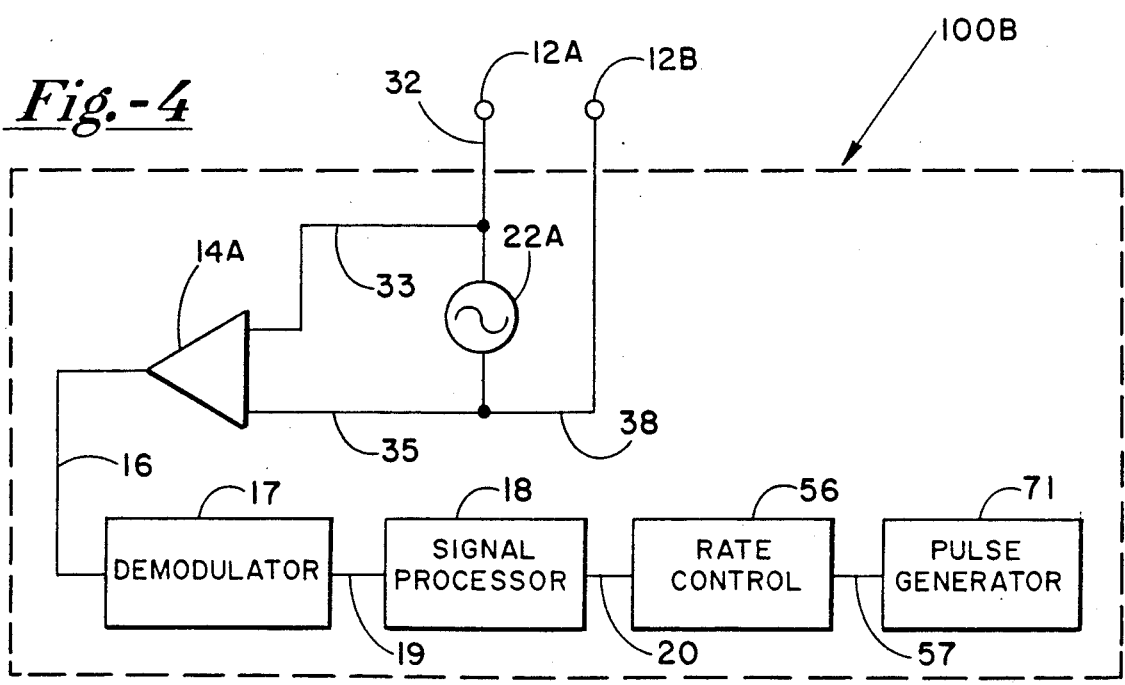
FIG. 4 shows a modified circuit employing the interface sensors of the invention.

Referring now to FIG. 4, a detailed diagram of an alternative embodiment of circuit 100B is shown. The circuit in FIG. 4 utilizes sensing electrodes 12A and 12B together as a single pair of sensing electrodes coupled to first and second inputs of amplifier means 14A. In this configuration, the can is not coupled to the amplifier means and the need for a second amplifier means is eliminated. The operation is similar to the configuration of 100A wherein the second sensing electrode is used instead of the pacer can 10.

Figure 5:
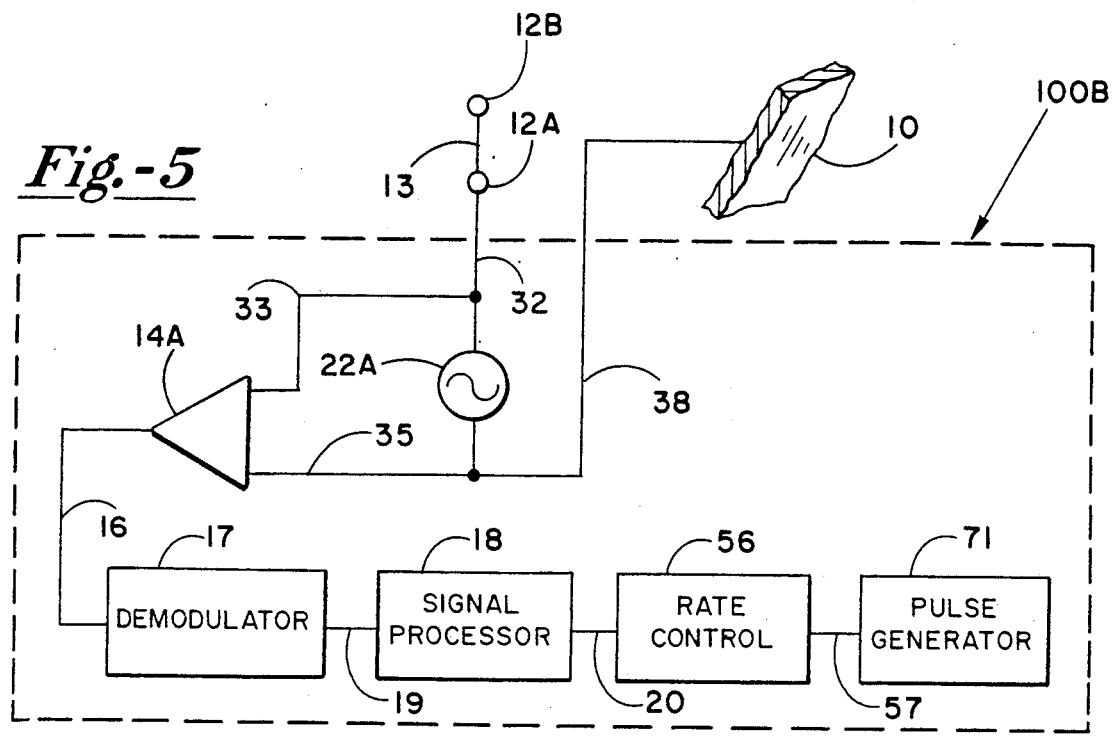
FIG. 5 shows a modified circuit employing the interface sensors of the invention shorted together.

Referring now to FIG. 5, yet another alternative embodiment of circuit 100B is shown in detail. In FIG. 5, interface sensing electrodes 12A and 12B are shorted together by conductor 13. In this way, changes in impedance signals which ocCur in first and second directions along the first and second sensing axes are simultaneously sensed by the pair of shorted interface electrodes and are carried on the same line to a first input of amplifier means 14A. The second input of amplifier 14A is connected via conductors 35 and 38 to the can 10. Downstream operation of the circuit of FIG. 5 is similar to that described with respect to circuits 100A and 100B hereinabove.

Figure 6:
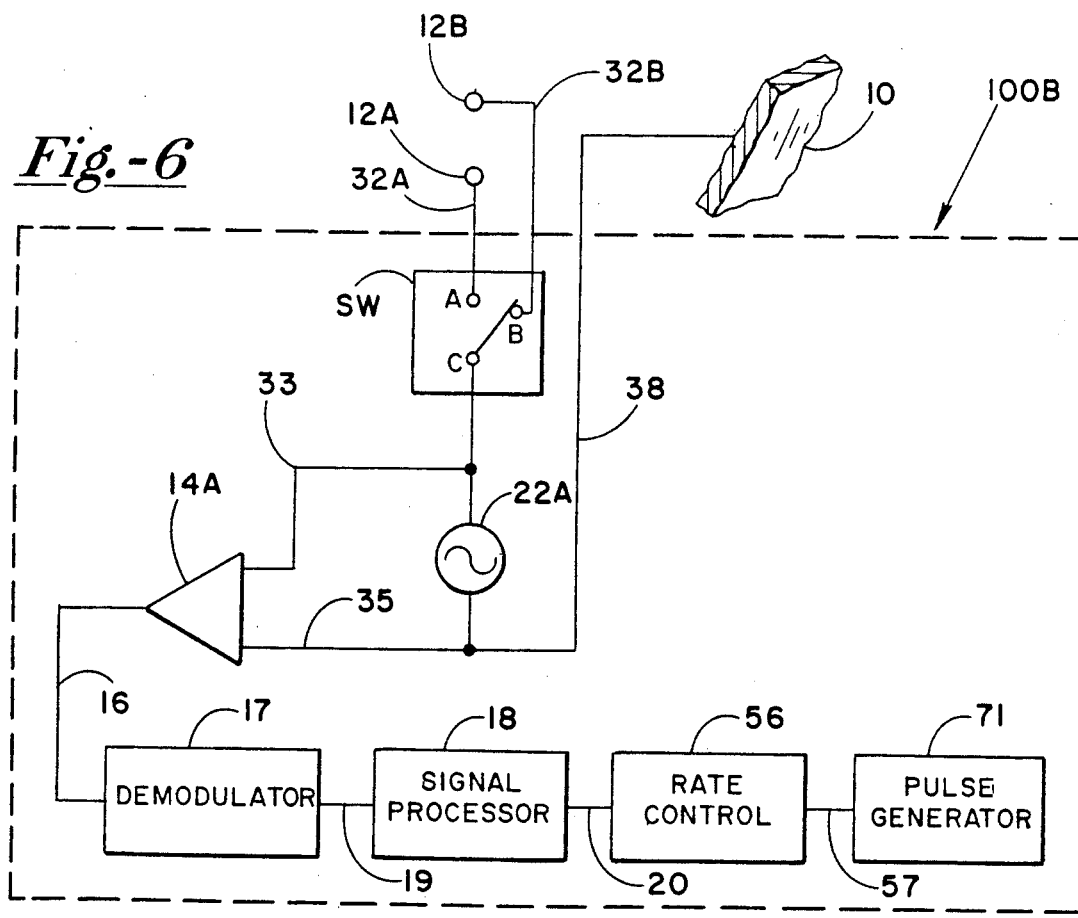
FIG. 6 shows yet another aspect of the invention employing a multiplexing approach.

Referring now to FIG. 6, yet another alternative embodiment of circuit 100B is shown employing a multiplexing approach. In FIG. 6, two interface sensing electrodes 12A and 12B are disposed on the pacemaker in a manner consistent with that shown in FIG. 1B. A single amplifying means 14A is connected to the common pole C of switch SW. Switch SW is preferably a solid state switching device which is switched via a switch control, such as a clock, which is not shown. Electrode 12A is connected by conductor 32A to a first pole A of the switch SW and the second interface electrode 12B is connected by connector 32B to a second pole B of switch SW. In operation, switch SW alternates switching the first input of amplifier means 14A through conductor 33 from pole A to pole B. Therefore, the signal introduced into the demodulator 17 is a signal which alternates between sensing movement in a first direction and sensing movement in a second direction. Such information can then be processed serially by the signal processor to provide a control current, proportional to the patient's movement, to the rate control means 56.

Having described the arrangement of the elements of the invention in considerable detail, it will prove beneficial to the understanding of the invention to now describe the operation of the invention. Referring now primarily to FIG. 3 with continuing reference to FIG. 2, note that the first and second interface sensing electrodes 12A and 12B each operate to form a first and second pair of sensing electrodes when each is individually paired with the metallic housing 10 of the pacer apparatus. As the patient moves, the amount and rate of movement will cause changes in high density current areas which immediately surround the first and second interface sensing electrodes. These high density current areas are generally indicated as areas 60 and 62 (shown in FIG. 1B). The impedance changes are carried as modulated signals to the first and second sense amplifiers 14A and 14B. The first and second sense amplifiers are coupled to the first and second pair of sensing electrodes respectively. The amplifier means receive and amplify the first and second modulated electrical signals developed across the sensing electrodes. These amplified modulated signals are then presented to the first and second demodulators 17A and 17B which demodulate the modulated carrier signals and recover the first and second modulating signals therefrom. The modulating signals are proportional to the impedance field around the first and second sensing electrodes which, in turn, are proportional to the patient's amount and rate of movement as is sensed in primarily a first direction by electrode 12A and primarily a second direction by electrode 12B.

The demodulated signals are then received by a signal processor means 18 which operates by conventional signal processing means to provide a processed signal proportional to the sensed movement via conductor 20 to the rate control means 56. Signal processing may be done using well known methods such as automatic gain control, peak detection and signal averaging techniques. The processed signal is then received by the rate control means 56 which responds to the processed signal by modifying the parameters controlling stimulating pulse rate, including attack and decay parameters, in a manner consistent with the movement exhibited by the patient as measured by the interface sensing electrodes. The rate control means provides a rate control signal so as to adjust the rate at which the pacer apparatus outputs stimulating pulses in a manner consistent with patient movement. The rate control means 56 provides the rate control signal to the pulse generator 71 which outputs pulses at a rate as determined by the rate control means. As those skilled in the art will appreciate, the circuitry of 100A operates in substantially the same manner except that only one interface signal from the first sensing electrode 12A is used.

It is believed that better overall sensing of the patient's movement can be accomplished using two or more interface sensing electrodes arranged in an orthogonal relationship. Although examples have been shown herein using one and two interface sensing electrodes, it may be possible, and in some cases even desirable, to have additional interface sensing electrodes with corresponding motion sensing circuitry included in the pacer apparatus. It will be understood by those skilled in the art that the motion sensing apparatus as provided by the present invention may operate in combination with a conventional pacemaker and also in combination with other rate adaptive techniques to provide a rate adaptive pacer apparatus which is responsive to the physical activity of the patient.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A variable rate cardiac pacer apparatus responsive to physical activity of a patient wherein the pacer includes a metal housing and wherein the apparatus comprises:
    (a) a first source of alternating current carrier signals of a first predetermined frequency coupled to the pacer housing;
    (b) a first sensing electrode having a first sensing axis disposed in a first direction, the first sensing electrode being insulated from the pacer housing, in electrical contact with body tissues and coupled to the carrier signals, wherein the first sensing electrode and the pacer housing are arranged to operate as a first pair of sensing electrodes across which first modulated electrical signals develop from impedance field changes around the first electrode;
    (c) first sense amplifier means coupled to the first pair of sensing electrodes for receiving and amplifying the first modulated electrical signals developed across the first pair of sensing electrodes;
    (d) first demodulator circuit means for demodulating the first modulated electrical signal and recovering a first demodulating signal therefrom, the first demodulating signal being proportional to the impedance field changes around the first sensing electrode which, in turn, are proportional to the patient's movement primarily in a first direction;
    (e) signal processing means for receiving the first demodulated signal and structured and arranged to provide processed signals which are proportional to the impedance field changes primarily in the first direction;
    (f) a rate control means for determining the rate at which heart stimulating pulses will be generated wherein the rate control means receives the processed signals and is structured and arranged to provide rate control signals consistent with the processed signals; and
    (g) pulse generator means responsive to the rate control signal for generating stimulating pulses at a rate consistent with the rate control signal.

2. The apparatus of claim 1 wherein the pacer housing includes a plastic top and the first sensing electrode resides exposed through the pacer housing's plastic top.

3. The apparatus of claim 1 further including:
    (a) a second source of alternating current carrier signals of a second predetermined frequency coupled to the pacer housing;
    (b) a second sensing electrode having a sensing axis arranged in a perpendicular relationship to the first sensing axis wherein the second sensing electrode and the pacer housing are structured and arranged to operate as a second pair of sensing electrodes wherein patient movement in a second direction is primarily sensed; and
    (c) a second sense amplifier means coupled to the second pair of sensing electrodes for receiving and amplifying a second set of modulated electrical signals developed across the second pair of sensing electrodes;
    (d) second demodulator circuit means for demodulating the first modulated electrical signal and recovering the first modulating signal therefrom, the first modulating signal being proportional to the impedance field changes around the first sensing electrode which, in turn, are proportional to the patient's movement primarily in a first direction; and (e) wherein the second set of amplified signals is presented to the second demodulator circuit for recovering a second modulating signal therefrom which is presented to the signal processing means for processing together with the first recovered modulating signal.

4. The apparatus of claim 3 wherein the pacer housing includes a plastic top and the first and second housing electrodes reside exposed through the pacer's housing's plastic top.

5. A method of operating a variable rate cardiac pacer apparatus responsive to physical activity of a patient, wherein the cardiac apparatus includes a pacer housing implanted in body tissues, comprising the steps of:

(a) sensing first electrical signals proportional to first impedance changes at a first interface between the pacer housing and body tissues around the pacer apparatus wherein the first electrical signals are modulated by alternating current carrier signals of a predetermined frequency in the range from about 500 to 10,000 Hertz; and (b) generating stimulating pulses having a rate adjusted to also be proportional to the impedance changes.

6. The method of claim 5 wherein the first impedance changes are proportional to patient movement primarily in a first direction, further including the steps of sensing second electrical signals proportional to second impedance changes at a second interface and generating stimulating pulses having a rate proportional to the first and second impedance changes.

7. Apparatus for measuring movement of a patient having an implanted device including a metal housing therein wherein the apparatus comprises:

(a) a first source of alternating current carrier signals of a first predetermined frequency in the range from about 500 to 10,000 Hertz coupled to the metal housing;

(b) a first sensing electrode having a first sensing axis disposed in a first direction, the first sensing electrode being insulated from the metal housing, in electrical contact with body tissues and coupled to the carrier signals, wherein the first sensing electrode and the metal housing are arranged to operate as a first pair of sensing electrodes across which first modulated electrical signals develop;

(c) first sense amplifier means coupled to the first pair of sensing electrodes for receiving and amplifying the first modulated electrical signals developed across the sensing electrodes; and (d) first demodulator circuit means for demodulating the first modulated electrical signal and recovering a first demodulated signal therefrom, said first demodulated signal being proportional to the impedance field changes around the first sensing electrode which, in turn, is proportional to the patient's movement primarily in a first direction.

8. The apparatus of claim 7 wherein the metal housing includes a plastic top and the first sensing electrode resides exposed through the plastic top.

9. The apparatus of claim 7 further including:

(a) a second source of alternating current carrier signals of a second predetermined frequency in the range from 500 to 10,000 Hertz coupled to the metal housing;

(b) a second sensing electrode having a sensing axis arranged in a perpendicular relationship to the first sensing axis, wherein the second sensing electrode and the metal housing are structured and arranged to operate as a second pair of sensing electrodes wherein patient movement in a second direction is primarily sensed; and (c) a second sense amplifier means coupled to the second pair of sensing electrodes for receiving and amplifying a second set of modulated electrical signals developed across the second pair of sensing electrodes and wherein the second set of amplified signals is presented to a second demodulator circuit for recovering a second modulated signal therefrom.

10. The apparatus of claim 9 wherein the pacer housing includes a plastic top and the first and second sensing electrodes reside exposed through the metal housing's plastic top.

11. A variable rate cardiac pacer apparatus responsive to the physical activity of a patient wherein the pacer includes a metal housing, and wherein the apparatus comprises:

(a) a first source of alternating current carrier signals of a first predetermined frequency;

(b) a first sensing electrode having a first sensing axis disposed in a first direction being insulated from the pacer housing, in electrical contact with body tissues and coupled to the carrier signals;

(c) a second sensing electrode having a second sensing axis wherein the first sensing electrode and the second sensing electrode are arranged to operate as a pair of sensing electrodes across which modulated electrical signals develop;

(d) sense amplifier means coupled to the pair of sensing electrodes for receiving and amplifying the modulated electrical signals developed across the sensing electrodes;

(e) demodulator circuit means for demodulating the modulated electrical signal and recovering a modulating signal therefrom, said modulating signal being proportional to the impedance field changes around the first sensing electrode which, in turn, is proportional to the patient's movement primarily in a first direction;

(f) signal processing means for receiving the first demodulated signal and structured and arranged to provide a processed signal which is proportional to the impedance field changes primarily in a first direction;

(g) a rate control means for determining the rate at which heart stimulating pulses will be generated wherein the rate control means receives the processed signal and is structured and arranged to provide a rate control signal consistent with the processed signal; and (h) pulse generator means responsive to the rate control signal for generating a stimulating pulse having characteristics consistent with the rate control signal.

12. The apparatus of claim 11 wherein the predetermined carrier frequency is a frequency in the range of about 500 to 10,000 Hertz.

13. A variable rate cardiac pacer apparatus responsive to physical activity of a patient wherein the pacer includes a metal housing and wherein the apparatus comprises:

(a) a first source of alternating current carrier signals of a first predetermined frequency coupled to the pacer housing;

(b) a first sensing electrode having a first sensing axis disposed in a first direction, insulated from the pacer housing, in electrical contact with body tissues and coupled to the carrier signals;

(c) a second sensing electrode having a second sensing axis which intersects the first sensing axis, wherein the first sensing electrode and the second sensing electrode are shorted together to operate as a pair of sensing electrodes;

(d) sense amplifier means coupled to the first pair of sensing electrodes at a first input and to the metal housing at a second input for receiving and amplifying modulated electrical signals developed across the sensing electrodes and the pacer housing;

(e) demodulator circuit means for demodulating the modulated electrical signals and recovering a modulating signal therefrom, the modulating signal being proportional to the impedance field changes around the first and second sensing electrodes which, in turn, are proportional to the patient's movement in first and second directions;

(f) signal processing means for receiving the demodulated signal and structured and arranged to provide a processed signal which is proportional to the impedance field changes primarily in the first and second directions;

(g) a rate control means for determining the rate at which heart stimulating pulses will be generated wherein the rate control means receives the processed signal and is structured and arranged to provide a rate control signal consistent with the processed signal; and (h) pulse generator means responsive to the rate control signal for generating a stimulating pulse having characteristics consistent with the rate control signal.

14. The apparatus of claim 13 wherein the pacer housing includes a plastic top and the first and second sensing electrodes reside exposed through the pulse generator's plastic top.

15. The apparatus of claim 13 wherein the alternating current carrier signals have a predetermined frequency in the range from about 500 to 10,000 Hertz.

16. A variable rate cardiac pacer apparatus responsive to physical activity of a patient wherein the pacer includes a metal housing and is coupled to stimulating electrodes, and where the apparatus comprises:

(a) a first source of alternating current carrier signals of a predetermined frequency coupled to the pacer housing;

(b) a switching means having a common terminal and first and second poles;

(c) a first sensing electrode having a first sensing axis disposed in a first direction, the first sensing electrode being insulated from the pacer housing, in electrical contact with body tissues and coupled to the carrier signals, wherein the first sensing electrode and the pacer housing are arranged to operate as a first pair of sensing electrodes across which first modulated signals develop when the switching means is in a first position;

(d) a second sensing electrode having a sensing axis arranged in a perpendicular relationship to the first sensing axis, wherein the second sensing electrode and the pacer housing are structured and arranged to operate as a second pair of sensing electrodes across which second modulated signals develop when the switching means is in a second switch position;

(e) sense amplifier means alternately coupled by the switching means to the first pair of sensing electrodes and the second pair of sensing electrodes for receiving and amplifying the first and second modulated signals developed across the first and second sensing electrodes in an alternating fashion;

(f) demodulator circuit means for alternately demodulating the first and second modulated signals and recovering a first demodulated signal and a second demodulated signal therefrom, the first and second demodulated signals being proportional to the impedance field changes around the first and second sensing electrodes respectively which, in turn, are proportional to the patient's movement in first and second directions;

(g) signal processing means for receiving the first and second demodulated signals and structured and arranged to provide a processed signal which is alternately proportional to the impedance field changes in the first and second directions;

(h) a rate control means for determining the rate at which heart stimulating pulses will be generated wherein the rate control means receives the processed signal and is structured and arranged to provide a rate control signal consistent with the processed signal; and (i) pulse generator means responsive to the rate control signal for generating a stimulating pulse having characteristics consistent with the rate control signal.

17. The apparatus of claim 16 wherein the predetermined carrier frequency is a frequency in the range from about 500 to 10,000 Hertz.

18. The apparatus of claim 17 wherein the pacer housing includes a plastic top and the first and second sensing electrodes reside exposed through the pacer housing's plastic top.

19. The apparatus of claim 16 wherein the switching means comprises a solid state switching device.

* * * * *

UNITED STATES PATENT AND TRADEMARK OFFICE
CERTIFICATE OF CORRECTION

PATENT NO. : 5,027,813

DATED : July 2, 1991

INVENTOR(S) : Brian D. Pederson and John A. Hauck

It is certified that error appears in the above-identified patent and that said Letters Patent is hereby corrected as shown below:

Column 7, lines 10-11, delete "housing" and put instead -- sensing --.

Signed and Sealed this

First Day of December, 1992

*Attest:*

DOUGLAS B. COMER

*Attesting Officer*     *Acting Commissioner of Patents and Trademarks*